United States Patent
Draper

(10) Patent No.: US 9,655,759 B2
(45) Date of Patent: May 23, 2017

(54) PROTECTIVE BRACES FOR JOINTS AND ASSOCIATED METHODS

(76) Inventor: Shane D. Draper, Elko, NV (US)

( * ) Notice: Subject to any disclaimer, the term of this patent is extended or adjusted under 35 U.S.C. 154(b) by 1386 days.

(21) Appl. No.: 12/852,380

(22) Filed: Aug. 6, 2010

(65) Prior Publication Data

US 2011/0034846 A1 Feb. 10, 2011

Related U.S. Application Data

(60) Provisional application No. 61/232,337, filed on Aug. 7, 2009.

(51) Int. Cl.
*A61F 5/00* (2006.01)
*A61F 5/01* (2006.01)

(52) U.S. Cl.
CPC .................................. *A61F 5/0111* (2013.01)

(58) Field of Classification Search
CPC .. A61F 5/0123; A61F 2005/0181; A61F 5/01; A61F 2002/745; A61F 2002/747; A61F 2005/0144; A61F 2005/0146; A61F 2005/0169; A61F 2/68; A61F 5/0102; A61F 5/0111; A61F 5/058; A61F 2005/0137

USPC ............. 602/23, 26, 27, 60, 62, 65; 128/882
See application file for complete search history.

(56) References Cited

U.S. PATENT DOCUMENTS

| | | | | |
|---|---|---|---|---|
| 5,944,678 A * | 8/1999 | Hubbard | ......................... | 602/27 |
| 6,929,617 B2 * | 8/2005 | McCormick et al. | .......... | 602/65 |
| 7,651,472 B2 * | 1/2010 | Gaylord et al. | ................ | 602/27 |
| 7,753,865 B1 * | 7/2010 | Hely | ............................... | 602/23 |

* cited by examiner

*Primary Examiner* — Michael Brown
(74) *Attorney, Agent, or Firm* — Durham Jones & Pinegar, P.C. Intellectual Property Law Group

(57) ABSTRACT

A brace for use in supporting a joint of a body of a subject is configured to provide the joint with a normal range of motion or a substantially normal range of motion while preventing abnormal and/or pathologic motion that might damage the joint or a connective band (e.g., a ligament, tendon, fascia, etc.) associated with the joint. The brace may include one or more engagement elements that engage a body part or body parts adjacent to the joint and one or more straps that are attached to the engagement element(s) at a location or locations that approximate the location(s) of one or more connective bands associated with the joint. The present invention also includes articles of clothing into which a brace is incorporated, as well as methods for supporting a joint.

12 Claims, 7 Drawing Sheets

PROTECTIVE BRACES FOR JOINTS AND ASSOCIATED METHODS

RELATED APPLICATION

This application claims priority to U.S. Provisional Application No. 61/232,337 filed Aug. 7, 2009 entitled PROTECTIVE BRACES FOR JOINTS AND ASSOCIATED METHODS, the entire application of which is incorporated herein by reference.

TECHNICAL FIELD

The present invention relates generally to apparatus for bracing joints of the body, or "braces," and, more specifically, to braces for stabilizing joints to prevent injury thereto while allowing for a full range of motion or a substantially full range of motion of at least one appendage associated with the joint. The present invention also relates to methods for preventing injury to joints of a subject's body.

RELATED ART

When an individual engages in athletic activities, it is sometimes desirable or even necessary for the individual to support one or more joints. A few techniques and mechanisms have been developed to at least temporarily provide joint support, including the use of athletic tape and braces.

Taping, if properly conducted, provides joint support without undesirably limiting the desired range of motion for the supported joint, but typically only remains effective for a few minutes at a time. Thus, if continued support is desired, the joint must be periodically retaped.

Generally, existing braces fit into two categories: (1) soft braces and (2) rigid braces. Soft braces, including neoprene supports, compression sleeves, and the like, are typically comfortable to wear. However, their comfort comes from their construction, which is usually not robust enough to provide much support.

When existing soft braces are configured in a manner that provides sufficient support to a joint, their construction often makes them uncomfortable. As an example, lace-up ankle braces typically fasten over the top of the foot. When worn for a prolonged period of time, the laces may (directly or from pressure applied by a shoe worn over the brace) numb the nerve that extends into the foot and restrict blood flow into and out of the foot. These affects often slow athletes down, causing many athletes to remove the brace when they should be wearing them.

Rigid braces usually work well, but are typically quite bulky and often uncomfortable. Conventionally, rigid braces have been used to support damaged and/or healing joints. Because of their intended use, many rigid braces limit the range of motion of the supported joint, often preventing desired movement—particularly during athletic activity. In addition, many rigid braces don't fit beneath clothing or, in the case of ankle braces, within shoes.

SUMMARY

In one aspect, the present invention includes braces for use with various joints of the body. A brace of the present invention may be configured to support and/or protect a joint from abnormal and/or pathologic motion while allowing the joint to move in a normal or substantially normal manner; i.e., in such a way that the joint has a full range of motion or a substantially full range of motion (e.g., 85%, 90%, 95%, or more) while it is supported and/or protected by the brace.

A brace of the present invention may be used in conjunction with any suitable joint of any suitable subject. Without limiting the scope of the present invention, one embodiment of a brace of the present invention may be configured for use with a human ankle. In other embodiments, a brace of the present invention may support a human knee. Of course, other embodiments of braces of the present invention may be designed and/or configured to support other joints of the human body (e.g., neck, shoulder, elbow, wrist, back, hip, etc.), as well as joints of the bodies of various animals.

In various embodiments, a brace according to the present invention includes one or more support straps that mimic the function of one or more bands of fibrous connective tissue (e.g., ligaments, tendons, fascia), which are referred to herein as "connective bands" for the sake of simplicity, of the joint with which the brace is to be used, which is referred to herein as a "corresponding joint" and as a "supported joint." Each support strap of a brace of the present invention may be configured, along with a remainder of the brace, to support a corresponding joint and to prevent injury to the corresponding joint. In some embodiments, the location of each support strap may approximate the location of its corresponding connective band in the body of a subject on which the brace is to be used. The tensile strength of a support strap may match or even exceed the tensile strength of its corresponding connective band.

In some embodiments, opposite ends of the one or more support straps of a brace of the present invention are secured to and extend between a pair of engagement members that are positioned and configured to engage (e.g., wrap around) body parts on opposite sides of the joint that is to be supported and protected. Thus, the one or more support straps may at least partially secure the engagement members to one another. In a specific embodiment of ankle brace that incorporates teachings of the present invention, the pair of engagement members is secured directly to one another at a first, central location. At second, lateral locations on opposite sides of the first, central location, the engagement members are spaced apart from one another, but secured to one another by support straps. In some embodiments, the configuration and relative association of the engagement members may shape the brace in such a way that it will receive and even conform or substantially conform to the shape of a body part adjacent to the supported joint, such as a heel adjacent to a supported ankle.

In a method of the present invention, a brace is positioned around a joint with at least one support strap aligned approximately over a connective band or group of connective bands to which the at least one support strap corresponds. One or more engagement members of the brace may be secured to a part (or parts) of the body located adjacent to the joint that is to be supported. In some embodiments, a first engagement member may be secured to a first body part on a first side of the joint that is to be supported (e.g., around a foot, etc.), while a second engagement member is secured to a second body part on a second side of the joint (e.g., around the tibia and fibula, or shin, of the subject, etc.).

With an embodiment of a brace that incorporates teachings of the present invention in place, the subject wearing the brace may participate in an activity in which movement around the joint is required. The brace may allow for, or enable, such movement without limiting or substantially limiting the joint from enabling a normal range of movement, or full range of motion. During normal motion, the brace is not in tension. When the range of motion is extended to or beyond a desired limit (e.g., abnormal motion, pathologic motion, etc., such as when an ankle begins to twist), one or more of the elements of the brace becomes tense, redistributing the potentially injurious load on the protected joint across the brace. When undesired motion occurs, the support straps and each engagement element may work together to prevent the joint from moving beyond its normal range. In this manner, the brace may prevent the straining or spraining of one or more connective bands associated with the supported joint.

Other aspects of the present invention, as well as features and advantages of various aspects of the present invention, will become apparent to those of ordinary skill in the art through consideration of the ensuing description, the accompanying drawings, and the appended claims.

DETAILED DESCRIPTION

Figure 1:
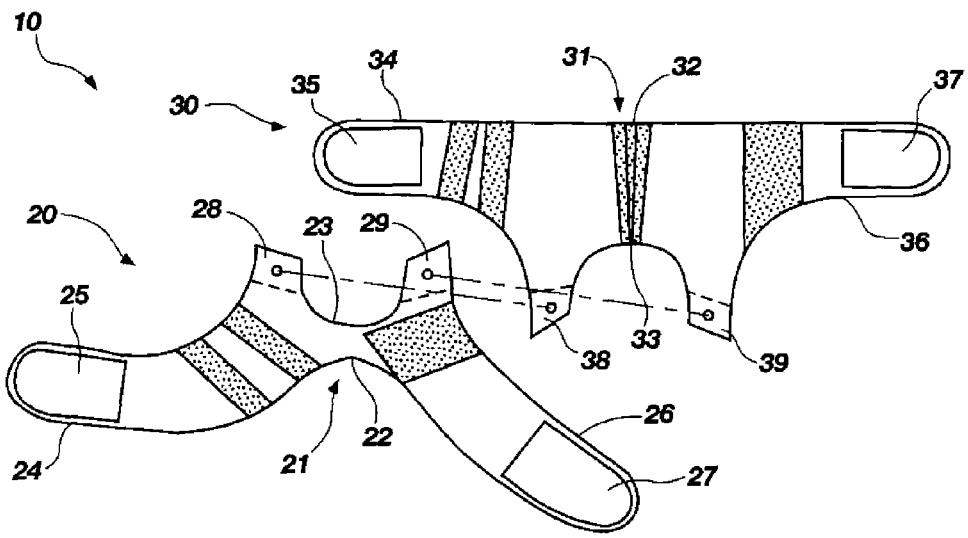
FIG. 1 illustrates an embodiment of brace of the present invention that is configured to support and/or protect an ankle of a human.
Figure 2:
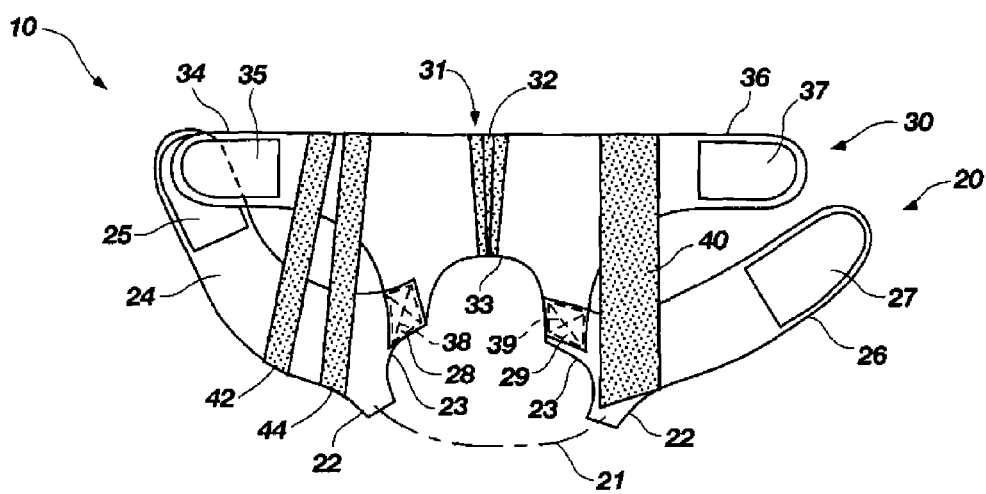
FIG. 2 depicts the two engagement members of the embodiment of brace shown in FIG. 1.

With reference to FIGS. 1 and 2, an embodiment of a brace 10 of the present invention is illustrated. Brace 10 includes a pair of engagement members 20 and 30 and a number of support straps 40, 42, 44. Engagement members 20 and 30 and support straps 40, 42, and 44 are configured and arranged to form a brace that supports and/or protects a human ankle.

A first engagement member 20 is configured to be secured around a subject's foot by wrapping around the subject's foot. In the illustrated embodiment, first engagement member 20 includes a central region 21 and a pair of elongate elements 24 and 26 that extend laterally, in opposite directions, from a first edge 22 of central region 21, imparting first engagement member 20 with a general "V" shape.

A second edge 23 of central region 21, which is opposite from first edge 22, may have a concave shape, and may be configured to accommodate at least a portion of the bottom of the heel of a subject's foot. The concave shape of second edge 23 may be configured to reduce or prevent the application of pressure to the heel of the subject's foot as first engagement member 20 is placed around and secured to the subject's foot.

Two protruding features 28 and 29 located at opposite ends of second edge 23 may facilitate the fastening of first engagement member 20 to corresponding features of second engagement member 30 (e.g., by sewing, etc.).

Second engagement member 30 is configured to wrap around the shin of a subject's leg. As shown in FIGS. 1 and 2, second engagement member 30 includes a central region 31 from which two elongate elements 34 and 36 extend, in opposite directions. As shown, elongate members 34 and 36 may be aligned or substantially aligned along a first edge 32 of central region 31. Central region 31 may, in some embodiments, be wider than each elongate element, with a second edge 33 of central region 31, which is opposite from first edge 32, having a concave shape. The concave shape of second edge 33 may be configured to accommodate a rear portion of the heel of the subject's foot.

Protruding features 38 and 39 located at opposite ends of second edge 33 (e.g., where corresponding edges of elongate members 34 and 36 taper toward and joint second edge 33) may facilitate the fastening (e.g., by sewing, etc.) of second engagement member 30 to first engagement member. More specifically, when first and second engagement members 20 and 30 are properly assembled, protruding features 28 and 29 may be superimposed with respect to protruding features 38 and 39, respectively, and the corresponding pairs of protruding features 28 and 38 and 29 and 39 fastened to one another.

First and second engagement members 20 and 30 may be configured and arranged relative to each other in such a way that they form a pocket for receiving a body part, such as the heel of the subject's foot.

In some embodiments, elongate elements 24 and 26 of first engagement member 20 may include complementary fasteners 25 and 27 that will engage one another to enable elongate elements 24 and 26 to secure first engagement member 20 around the subject's foot (e.g., around the midtarsal joint of the foot). Various embodiments of fasteners 25 and 27 include, but are not limited to, corresponding hook and loop fastener elements, complementary clips, a strap and buckle, or the like.

Likewise, some embodiments of second engagement member 30 may include elongate elements with complementary fasteners 35 and 37 that will engage one another to enable elongate elements 34 and 36 to secure second engagement member 30 around the subject's shin. Various embodiments of fasteners 35 and 37 include, but are not limited to, corresponding hook and loop fastener elements, complementary clips, a strap and buckle, or the like.

First and second engagement elements 20 and 30 may be formed from any suitable, flexible material that will enable them, and brace 10, to be securely arranged and secured in place over a joint, such as an ankle. The material from which first and second engagement elements 20 and 30 is formed may resist stretching and may have sufficient strength to withstand normal (and above-normal) and repeated forces applied thereto by the joint and/or body parts to which or over which brace 10 is to be secured. A variety of fabrics may be suitable for these purposes, including nylon, which is formed from polyamide fibers, as well as fabrics formed from other synthetic materials and from and natural fibers, and flexible non-fibrous sheets (e.g., polymeric films, etc.).

Support strap 40 is arranged in such a way that it spans a gap between spaced apart elongate elements 24 and 34, with its ends being secured (e.g., sewn, etc.) to elongate elements 24 and 34, while support straps 42 and 44 span a gap between spaced apart elongate elements 26 and 36, with their ends being secured (e.g., sewn, etc.) to elongate elements 26 and 36. The positions of support straps 40, 42, and 44 are configured to approximate the positions of corresponding connective bands spanning a joint in the body of a subject y whom brace 10 is to be worn. The length of each support strap 40, 42, 44, as well as its position relative to first and second engagement elements 20 and 30, may be tailored to prevent undesired movement (i.e., movement beyond the normal range of motion) of the supported joint or of one or more body parts located adjacent to the joint, the movement of which may be enabled by the joint.

In the depicted example, where the joint that is to be supported is an ankle, support strap 40 is positioned to support connective bands (e.g., the posterior talotibial ligament, the deltoid ligament, etc.) on the medial side (i.e., inside) of the ankle and foot, while support straps 42 and 44 are positioned to support connective bands (e.g., the calcaneofibular ligament, etc.) on the lateral side (i.e., outside) of the foot and ankle. Thus, the depicted brace 10 is configured for use with a subject's right foot, while a brace that is configured for use with the subject's left foot would be a mirror image of that depicted in FIGS. 1 and 2.

Each support strap 40, 42, 44 may be made of a material with adequate flexibility to enable the support joint to move about a normal or substantially normal range of motion, but sufficient tensile strength to withstand the potentially damaging forces that may be applied to the connective bands that are associated with the supported joint. In some embodiments, each support strap 40, 42, 44 may withstand several times (e.g., about seven times to about twelve times) a subject's body weight through the cross-sectional area of one or more connective bands in the supported joint. This may amount to several hundred pounds per square inch (psi) tensile force in some embodiments, or even to thousands of psi (e.g., about 5,000 psi to about 7,000 psi, etc.). Various embodiments of materials that may impart support straps 40, 42, 44 with these and potentially other desired properties include fabrics made from ballistic nylon fibers, from polyparaphenylene terephthalamide fibers, such as those marketed by E. I. du Pont de Nemours and Company of Carneys Point, N.J., as KEVLAR®, or from fibers of other suitable materials.

Figure 3:
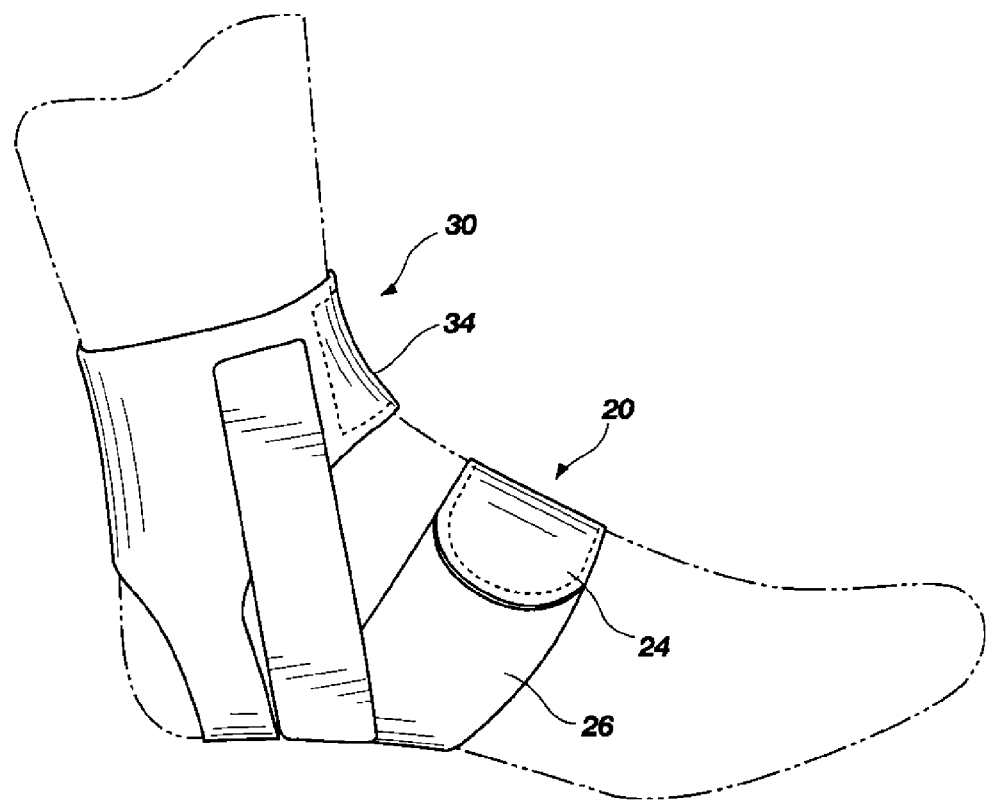
FIGS. 3 through 5 show the embodiment of brace illustrated by FIG. 1 around a human ankle.
Figure 4:
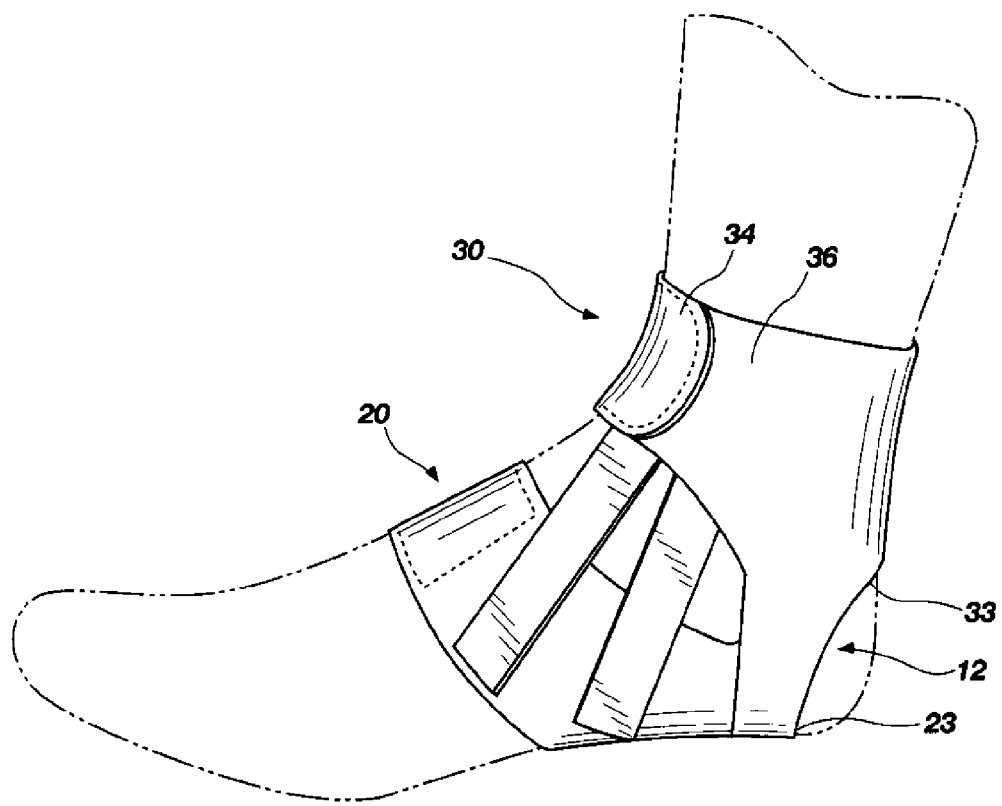
Figure 5:
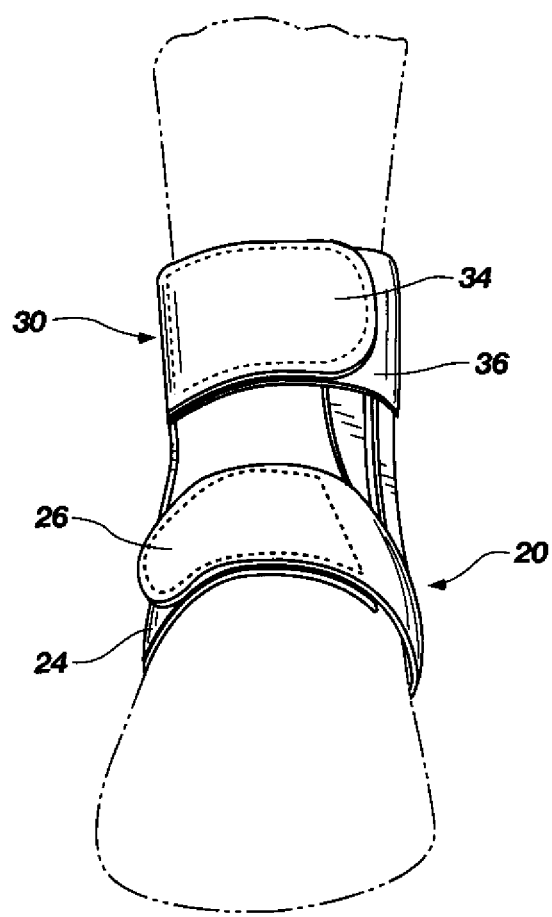

With added reference to FIGS. 3 through 5, in an embodiment of use, brace 10 is positioned beneath the appropriate foot of a subject (the right foot of a subject in the depicted embodiment), with first engagement element 20 positioned beneath the subject's foot and second engagement element positioned behind the subject's foot. The heel of the subject's foot may be positioned over or within a pocket 12 formed by the concave second edges 23 and 33 of central elements 21 and 31 (FIGS. 1 and 2) of first and second engagement elements 20 and 30, respectively, as shown in FIGS. 3 and 4. Elongate elements 24 and 26 of first engagement element 20 may be brought up around opposite sides of the foot and snugly, but comfortably, secured to one another over the foot, as illustrated by FIGS. 3 and 5. Elongate elements 34 and 36 of second engagement element 30 may be brought forward around opposite sides of the subject's shin and secured to one another so as to snugly, but comfortably engage an anterior (i.e., front) surface of the subject's shin, as shown in FIGS. 4 and 5.

As the subject engages in activity that results in the movement of the supported joint, brace 10 enables the subject to enjoy a full or substantially full range of motion at the supported joint, while preventing movement of the joint beyond or substantially beyond (e.g., far enough to strain any connective bands associated with the supported joint, etc.) its normal or desired range of motion. In some embodiments, brace 10 will absorb and distribute forces that are applied to the joint to the more robust body parts located on opposite sides of the joint. This redistribution may prevent undesired movement even when high loads (e.g., thousands of psi, etc.) are applied to the joint.

FIGS. 6 through 10 depict various alternative embodiments of braces that are configured to support and/or protect a human ankle.

Figure 6:
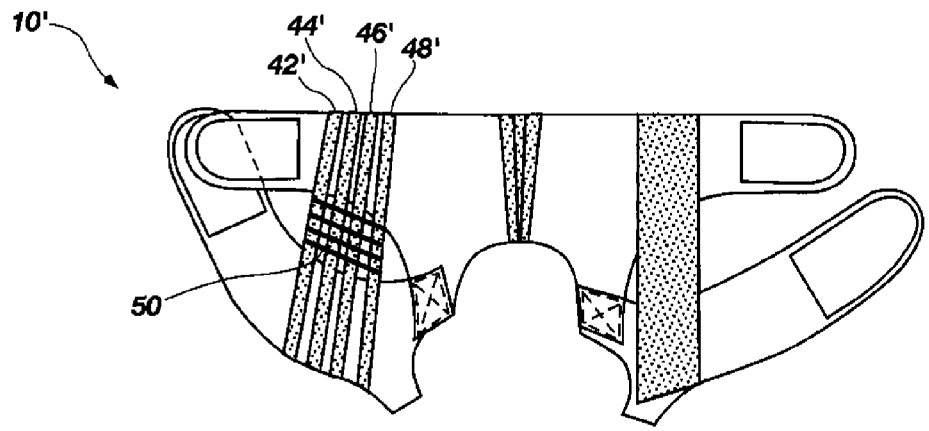
FIGS. 6 through 10 depict various alternative embodiments of ankle braces of the present invention.

The brace 10' of FIG. 6 includes four thin support straps 42', 44', 46', and 48' in place of support straps 42 and 44 of brace 10 (FIGS. 1, 2, and 4). Support straps 42', 44', 46', and 48' may be held in place relative to one another by way of one or more retention elements 50, which extend in a direction that is transverse to the directions in which support straps 42', 44', 46', and 48' extend.

Figure 7:
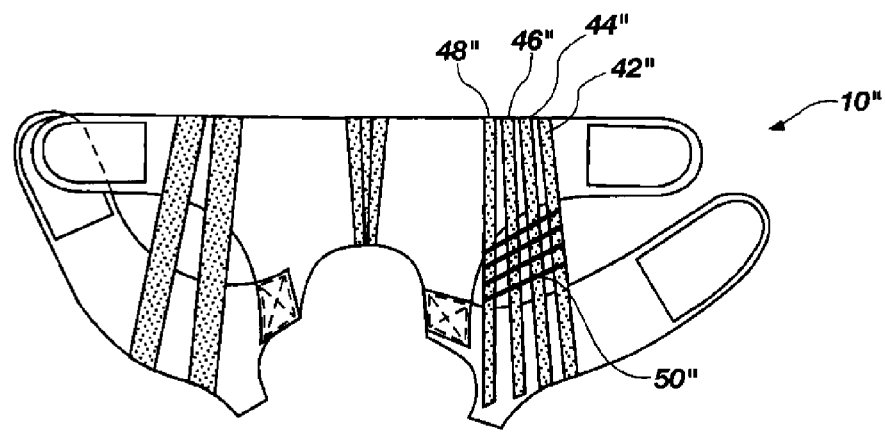

FIG. 7 depicts a brace 10" that includes a plurality of support straps 42", 44", 46", and 48" in place of support strap 40 (FIGS. 1, 2, and 3). One or more retention elements 50" may extend across support straps 42", 44", 46", and 48" to hold the same in place relative to one another.

Figure 8:
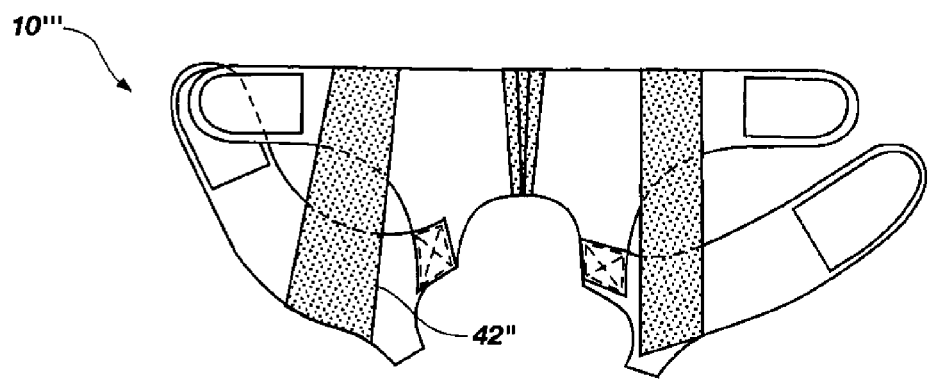

In FIG. 8, an embodiment of brace 10''' is shown that includes a single support strap 42''' in place of support straps 42 and 44 of brace 10 (FIGS. 1, 2, and 4).

Figure 9:
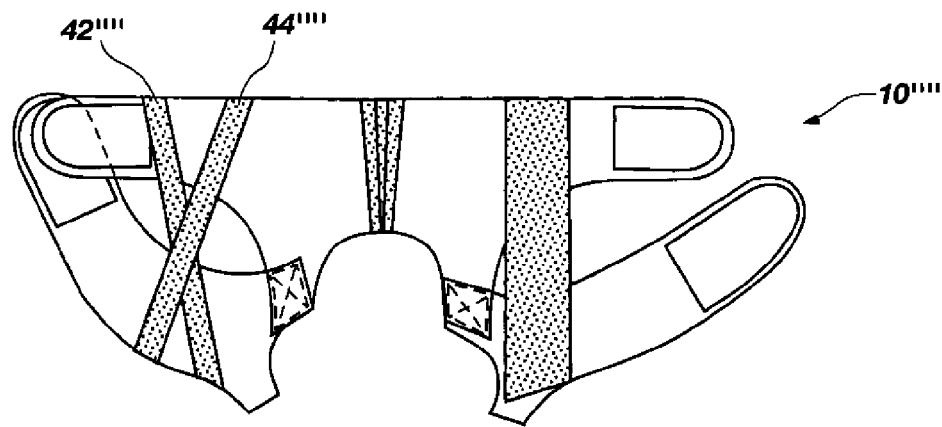

In the embodiment of brace 10'''' illustrated by FIG. 9, support straps 42 and 44 of brace 10 (FIGS. 1, 2, and 4) are replaced by a pair of intersecting, or crossed support straps 42'''' and 44''''.

Figure 10:
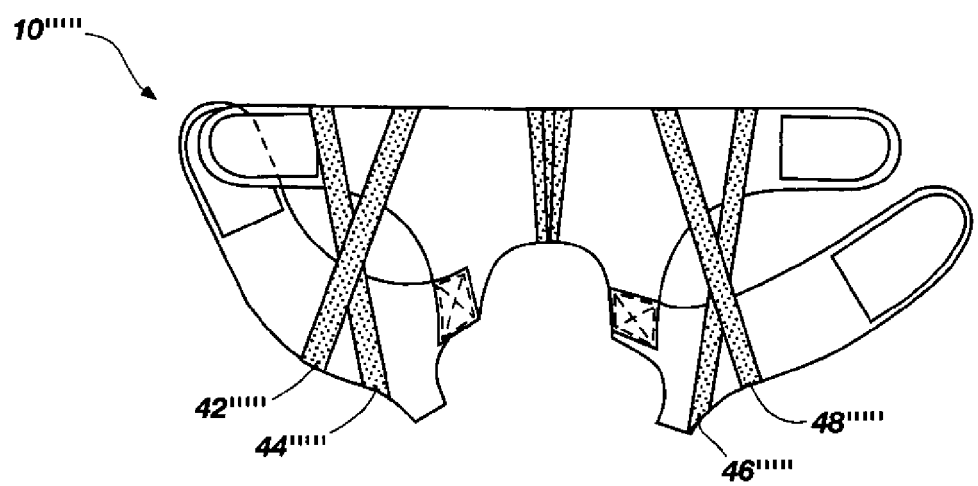

FIG. 10 illustrates an embodiment of brace 10''''' with two pairs of crossed support straps 42''''' and 44''''' and 46''''' and 48''''', with one pair on each side of brace 10'''''.

Figure 11:
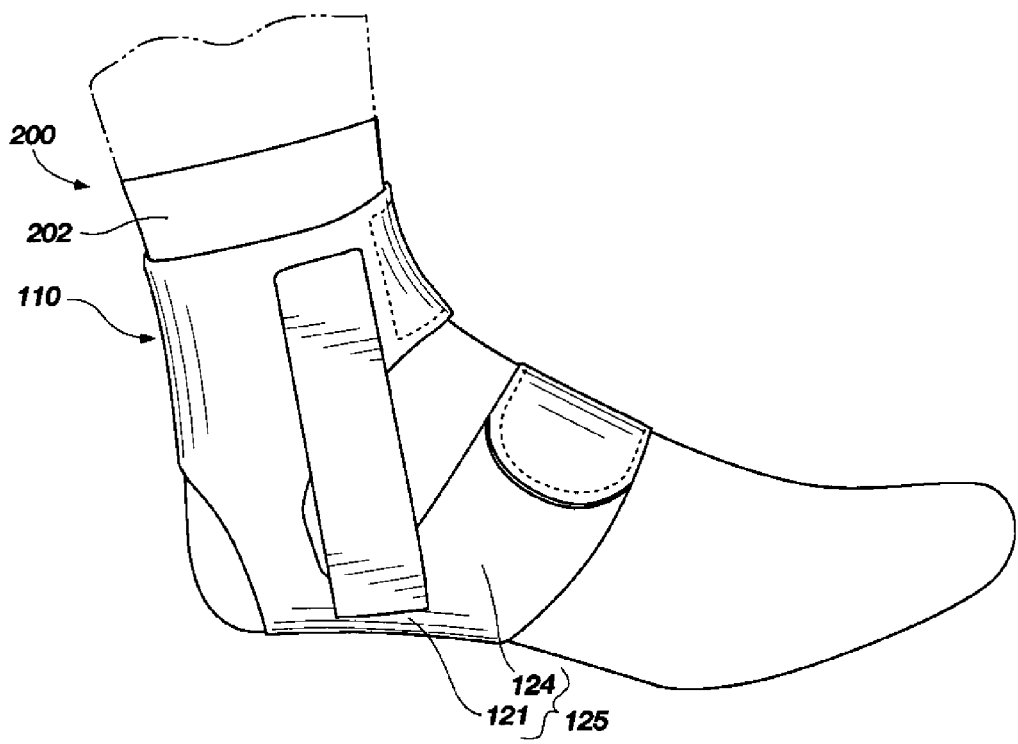
FIGS. 11 and 12 illustrated embodiments of socks that incorporate teachings of the present invention.

Turning now to FIG. 11, an embodiment of a sock 200 into which a brace 110 of the present invention has been incorporated is shown. In the depicted embodiment, brace 110 is carried by an exterior surface 202 of sock 200. In other embodiments, such as those represented by FIG. 12, a brace 110 may be partially carried within an interior surface 204 of a sock 200' or between layers of sock 200'.

While brace 110 may be configured as the above-described brace 10 (in reference to FIGS. 1 through 5), another embodiment of brace 110 is shown in FIG. 11. In the depicted embodiment, brace 110 differs from brace 10 in that first engagement element 120 includes a loop 125 formed by central region 121 and a single elongate element 124 through which a subject's foot may be introduced and removed. In some embodiments, loop 125 may have a size that enables it to be secured in place around a foot of a particular size to provide brace with a desired amount of stability without causing discomfort to the subject's foot. Loop 125 may, in some embodiments, be formed from a stretchable, resilient (e.g., elastic) material.

Figure 12:
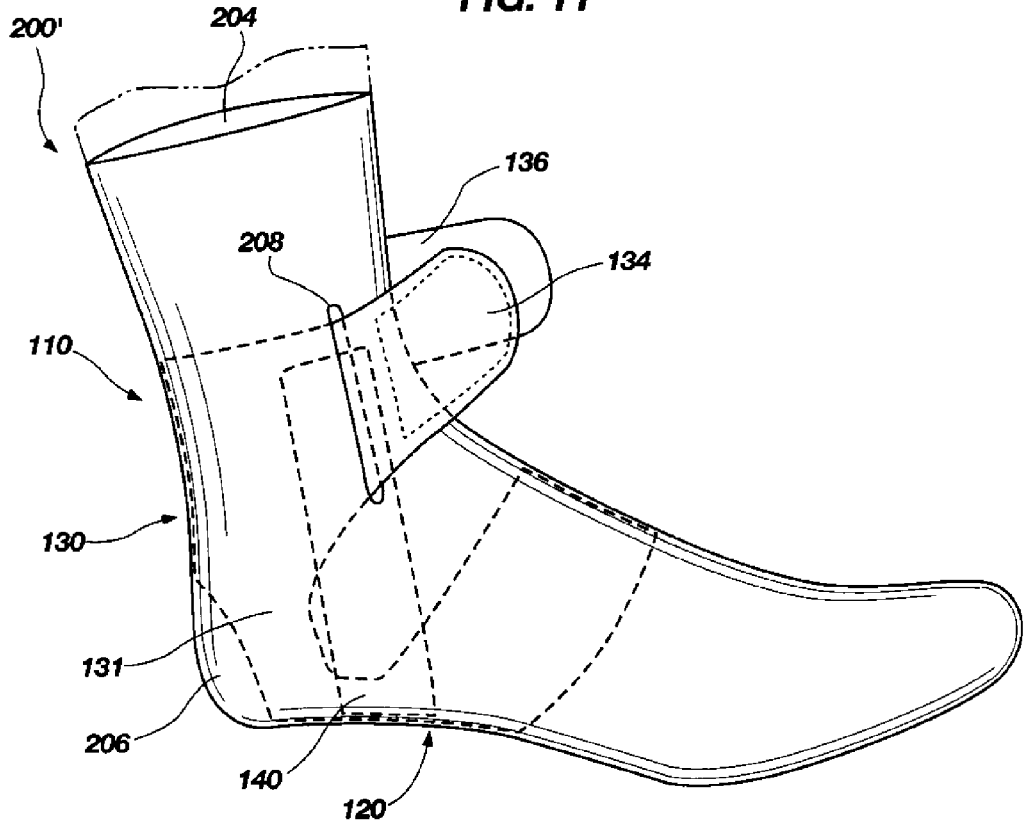

FIG. 12 illustrates an embodiment of a sock 200' in which a portion of a brace 110 is internally integrated. In the depicted embodiment, a first engagement element 120 of brace is located within an interior of sock 200', as are its support straps 140 and the central region 131 of its second engagement element 130. Elongate elements 134 and 136, or at least portions thereof, extend through apertures 208 that are located above the heel 206 of sock 200', enabling their use in tightening and securing brace 110 over a subject's ankle once sock 200' is in place on the subject's foot.

Figure 13:
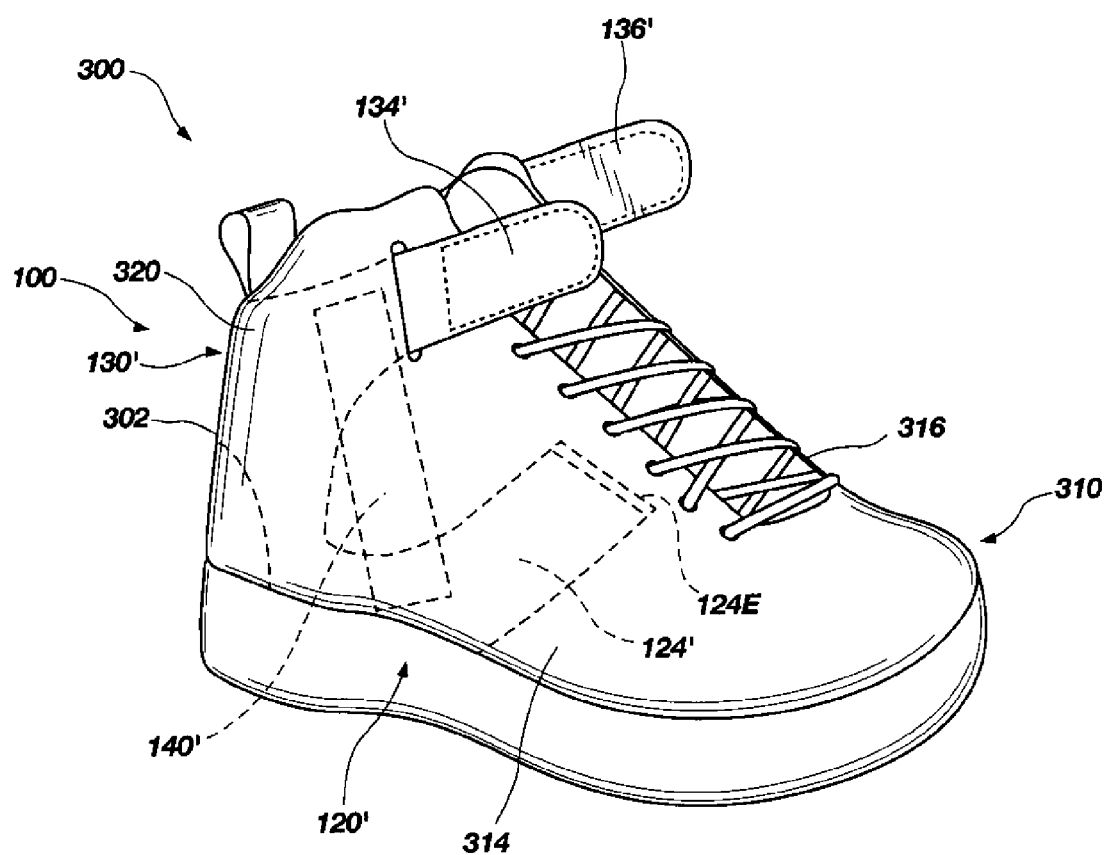
FIG. 13 depicts a shoe that includes an integrated embodiment of a brace of the present invention.

Referring now to FIG. 13, an embodiment of a shoe 300 (an athletic shoe in the depicted embodiment) into which an embodiment of a brace 110' of the present invention is incorporated is illustrated. Brace 110' is configured much like brace 10 (FIGS. 1 through 5), and includes first and second engagement elements 120' and 130' and straps 140' in substantially the same arrangement as their corresponding features of brace 10.

Straps 140' may be located within the interior of shoe 300, or they may be incorporated within the interior of an upper 310 of shoe 300.

Instead of being secured directly to one another, first and second engagement elements 120' and 130' of brace 110' may be secured to some other element of shoe 300, but in place relative to one another.

Elongated elements 124' and 126' (not shown) of first engagement element 120' may be truncated, with their ends 124E and 126E (not shown) lacking fasteners and instead being secured (e.g., sewn, etc.) into opposite sides 314 and 316 of upper 310 of shoe 300. With this arrangement, when shoe 300 is secured to a subject's foot (e.g., by tying, etc.), first engagement element 120' is secured snugly to the subject's foot.

Engagement elements 134' and 136' may likewise be associated with a heel collar 320 of shoe 300 and accessible from an exterior 302 of shoe 300 so that when shoe 300 has been secured to a subject's foot, engagement elements 134' and 136' may be fastened around the subject's shin.

Of course, other embodiments of braces according to the present invention may be incorporated into other pieces of athletic gear, or multiple embodiments of braces may be incorporated into a single piece of athletic gear (e.g., a compression shirt, compression shorts or pants, body armor, etc.).

Although the foregoing description contains many specifics, these should not be construed as limiting the scope of the present invention, but merely as providing illustrations of some embodiments. Similarly, other embodiments of the invention may be devised which do not exceed the scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A brace for a joint of a body of a subject, comprising:
   a first engagement element capable of being secured around a first body part of a subject adjacent to a first side of a joint of a body of the subject;
   a second engagement element capable of being secured around a second body part of the subject adjacent to a second side of the joint a portion of a top edge of the second engagement element continuous with or overlapping and fixed to a portion of a bottom edge of the first engagement element; and
   a plurality of flexible support straps extending from the first engagement element to the second engagement element, positions and orientations of each flexible support strap of the plurality of flexible support straps on the brace approximating locations and orientations of a plurality of connective bands of the joint in the body of the subject, first ends of the plurality of flexible support straps located a first distance from one another on the first engagement element, second ends of the plurality of flexible support straps being positioned a second distance apart from one another on the second engagement element, the second distance being greater than the first distance,
   the first engagement element, the second engagement element, and the plurality of flexible support straps configured and arranged to enable full range of motion of the joint while preventing abnormal motion of the joint.

2. The brace of claim 1, wherein the first engagement element, the second engagement element, and the plurality of flexible support straps are configured and arranged to distribute a load applied to the plurality of flexible support straps from the plurality of flexible support straps to the first engagement element and the second engagement element.

3. The brace of claim 1, wherein the plurality of flexible support straps comprises a material that will withstand a tensile load of at least thousand pounds per square inch.

4. The brace of claim 3, wherein the plurality of flexible support straps comprises poly-paraphenylene terephthalamide fibers or ballistic nylon.

5. The brace of claim 1, wherein flexible support straps of the plurality of flexible support straps are located to approximate locations of connective bands on different sides of the joint in the body of the subject.

6. The brace of claim 5, wherein the first engagement element and the second engagement element are in fixed positions relative to one another.

7. The brace of claim 6, wherein the first engagement element is configured to engage part of a foot of the subject and the second engagement element is configured to engage a shin of the subject.

8. The brace of claim 7, wherein a first flexible support strap of the plurality of flexible support straps is located on a lateral side of the brace and a second flexible support strap of the plurality of support straps is located on a medial side of the brace.

9. The brace of claim 1, wherein at least one of the first engagement element and the second engagement element and at least one flexible support strap of the plurality of flexible support straps are elastic.

10. The brace of claim 1, wherein the first engagement element and the second engagement element are configured to receive at least a portion of a load applied to at least one flexible support strap of the plurality of flexible support straps and to redistribute at least the portion of the load to body parts to which the first engagement element and the second engagement element are secured.

11. The brace of claim 1, further comprising:
    at least one retention element securing at least two flexible support straps of the plurality of flexible support straps to one another, the at least one retention element extending transversely across at least portions of the at least two flexible support straps.

12. The brace of claim 11, wherein the at least one retention element is secured to locations of the at least two flexible support straps at intermediate locations between first ends of the at least two flexible support straps and second ends of the at least two flexible support straps.

* * * * *